(12) United States Patent
Walzman

(10) Patent No.: US 10,576,245 B2
(45) Date of Patent: Mar. 3, 2020

(54) BYPASS CATHETER

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 0 days.

(21) Appl. No.: 16/100,351

(22) Filed: Aug. 10, 2018

(65) Prior Publication Data
US 2019/0217053 A1    Jul. 18, 2019

Related U.S. Application Data

(63) Continuation of application No. 15/932,911, filed on May 18, 2018, which is a continuation-in-part of application No. 15/732,953, filed on Jan. 16, 2018.

(51) Int. Cl.
| | |
|---|---|
| *A61M 25/00* | (2006.01) |
| *A61M 25/10* | (2013.01) |
| *A61N 7/00* | (2006.01) |
| A61M 5/14 | (2006.01) |
| A61B 17/12 | (2006.01) |

(52) U.S. Cl.
CPC .......... *A61M 25/007* (2013.01); *A61M 25/10* (2013.01); *A61N 7/00* (2013.01); *A61B 17/12136* (2013.01); *A61M 5/14* (2013.01); *A61M 2025/0073* (2013.01); *A61M 2025/0076* (2013.01); *A61M 2025/105* (2013.01); *A61M 2025/1095* (2013.01)

(58) Field of Classification Search
CPC .. A61M 2025/0197; A61M 2025/1097; A61M 2025/1095; A61B 17/3207; A61B 2017/22079; A61B 2017/22084
See application file for complete search history.

(56) References Cited

U.S. PATENT DOCUMENTS

| | | | |
|---|---|---|---|
| 4,573,966 A | * 3/1986 | Weikl | A61M 25/1011 604/101.05 |
| 4,755,176 A | 7/1988 | Patel | |
| 4,784,638 A | 11/1988 | Ghajar et al. | |
| 4,968,306 A | * 11/1990 | Huss | A61M 25/007 604/264 |
| 4,970,926 A | 11/1990 | Ghajar et al. | |
| 5,180,387 A | 1/1993 | Ghajar et al. | |
| 5,370,617 A | * 12/1994 | Sahota | A61M 25/104 604/102.02 |

(Continued)

*Primary Examiner* — Emily L Schmidt

(57) ABSTRACT

An innovative medical device that permits rapid, minimally invasive restoration of blood flow across a vascular blockage. A method employing said device, allowing for lysis or removal of said blockage. Said device creates a temporary bypass using longitudinal structure configured for insertion into the blood vessel and adapted to deliver a side hole to a target area. The side hole defines a distal first segment and a proximal second segment with a lumen to allow blood flow therethrough to the distal end hole. In an alternate embodiment, a slidable outer sheath can cover the side hole to permit reversal of blood flow from the distal end hole to a proximal end hole located outside a patient's body by means of an aspiration controller. Alternate embodiments include an optional anchoring balloon, a macerating stent or wires, perforations for fluid delivery, and a backflow valve.

24 Claims, 5 Drawing Sheets

(56) References Cited

U.S. PATENT DOCUMENTS

| | | | |
|---|---|---|---|
| 5,460,610 A * | 10/1995 | Don Michael | A61M 25/0133 |
| | | | 604/101.03 |
| 5,800,407 A | 9/1998 | Eldor | |
| 5,954,687 A | 9/1999 | Baudino | |
| 6,223,637 B1 | 5/2001 | Hansen | |
| 6,364,900 B1 * | 4/2002 | Heuser | A61B 17/12109 |
| | | | 606/194 |
| 8,403,911 B2 | 3/2013 | Adams et al. | |
| 8,496,629 B2 | 7/2013 | McKinnon et al. | |
| 9,364,634 B2 | 6/2016 | Adams et al. | |
| 9,399,112 B2 | 7/2016 | Shevgoor et al. | |
| 9,440,043 B2 | 9/2016 | Arora et al. | |
| 2008/0125746 A1 * | 5/2008 | Shapland | A61M 25/10 |
| | | | 604/508 |
| 2012/0302953 A1 * | 11/2012 | Don Michael | A61B 17/22 |
| | | | 604/101.05 |
| 2013/0158511 A1 * | 6/2013 | Aggerholm | A61B 17/3207 |
| | | | 604/509 |
| 2017/0000493 A1 * | 1/2017 | Boehm, Jr. | A61B 17/12136 |
| 2018/0161552 A1 * | 6/2018 | Larson | A61M 25/0026 |

* cited by examiner

BYPASS CATHETER

CROSS-REFERENCES

This is a continuation application claiming priority to the continuation-in-part application Ser. No. 15/932,911 filed May 18, 2018 (18 May 2018) which, in turn, claims the benefit of priority to nonprovisional utility application Ser. No. 15/732,953 filed Jan. 16, 2018 (16-JAN.-2018).

BACKGROUND OF THE INVENTION

Field of the Invention

The present invention relates generally to medical device placed in a minimally invasive manner, most often percutaneous and endovascular; specifically, to a bypass catheter to ameliorate ischemic injury.

Discussion of the Prior Art

The use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply.

One of the problems associated with using balloons is that although control of the blood flow through a portion of the blood vessel is achieved, including blockage of the blood supply to a targeted site, blood flow is completely interrupted to other sites near the targeted site. This shortcoming can be tolerated for a short duration because when one blood vessel becomes blocked, the body normally increases the blood flow through other, essentially paralleling blood vessels. However, complex medical procedures may not be achieved during said short duration resulting in injury to said other sites or requiring multiple operations at the same targeted site. Additionally, current bypass catheters are designed to be surgically implanted, which is not practical for immediate relief of progressive ischemia caused by a sudden blockage of a blood vessel, such as from a thrombus or embolus.

The present invention surmounts the problem of complete blood interruption that causes ischemia, which if not rapidly reversed will result in permanent injury.

SUMMARY OF THE INVENTION

The present invention provides an improved catheter, for use in the blood vessel system in the body, which invention includes a catheter device and method of use.

The present invention combines a temporary bypass balloon, the single lumen difficult access support catheter, and the rotating irrigating and aspirating thrombectomy device. These are disclosed in Ser. No. 15/732,397 (temporary bypass balloon catheter); and Ser. Nos. 15/258,877, 15/538,898, and 15/731,478 (rotating separator, irrigator microcatheter for thrombectomy); and other Walzman single-lumen support disclosures. The present invention is deployed to address a clot in artery or vein that is causing ischemia or heart strain because of the lack of flow through.

The present invention is capable for being positioned so that the side hole of the present inventions is located on one side of said artery or vein clot/blockage and the end hole of the present invention is located on the other side of the said artery or vein clot/blockage. Once the present invention is positioned, a bypass element of the present invention will allow temporary bypass of flow through the catheter, through the first segment of the catheter.

In order to prevent backflow of the blood into the second segment of the catheter, the catheter would either have a valve, a smaller proximal diameter, or be attached to a pressurized fluid line, or a combination of the above. Additionally, the catheter can have a second lumen in either of the two previously described arrangements that instead of delivering fluid into a balloon, as described in the above-mentioned bypass balloon invention, would deliver fluid into the clot between the side hole and the and hole. This would allow delivery of lytics or other such medications into the clot while there is an effective temporary bypass of flow through the catheter, allowing time for the directly applied medication to break up the clot and dissolve the clot while avoiding ischemic tissue injury during the interim time. Some embodiments, which have a balloon on the outer diameter as well, can comprise at least a third lumen as well.

Additionally, the present invention can have additional side loops that can macerate the clot when the catheter is rotated. Aspiration can also be applied to the catheter, which can allow aspiration through the side hole and or through the end hole. If aspiration through the end hole only is desired then the side hole can be withdrawn into a sheath so that there is no aspiration on the side hole and all aspiration forces on the end hole. Alternatively, an actively controlled valve can close said side hole.

Some embodiments can have a complex shape to the second catheter segment, wherein rotation of the catheter itself can cause maceration. One example of such a complex shape is a sinusoidal shape.

Additionally, if there is a desire to arrest flow and or reverse flow during the maceration process to prevent Downstream showering of clots, an additional optional balloon on the catheter or the sheath can be inflated, as depicted by 50.

There is a critical advantage to this device in that allows rapid restoration of temporary flow of blood through a blockage to avoid ischemic injury, with immediate restoration of a degree of flow beyond a clot. This will allow additional time to remove or dissolve the clot while allowing flow to the at-risk tissue. Additionally, in the case of pulmonary emboli which are large, there is an additional issue of heart strain due to the lack of outflow from the right side of the heart. The temporary bypass catheter described here can also help relieve such heart strain by allowing outflow from the right heart past said clot when there are large pulmonary emboli in the main pulmonary arteries.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

The present invention combines elements of three prior inventions by Walzman, namely a temporary bypass catheter and balloon, a single lumen support catheter, and the rotating irrigating and aspirating thrombectomy device.

The current invention is composed of a catheter with at least one distal end hole, and at least one bypass window proximal to said end hole. The present invention is capable of deploying said catheter across a blockage in a vessel.

The temporary balloon element, when present on the bypass catheter, is composed of a catheter with at least one distal end hole, at least one bypass window proximal to said end hole and a balloon element between said end hole and said bypass window. The present invention is capable of deploying said balloon element, before inflation, across a blockage in a vessel.

Figure 1:
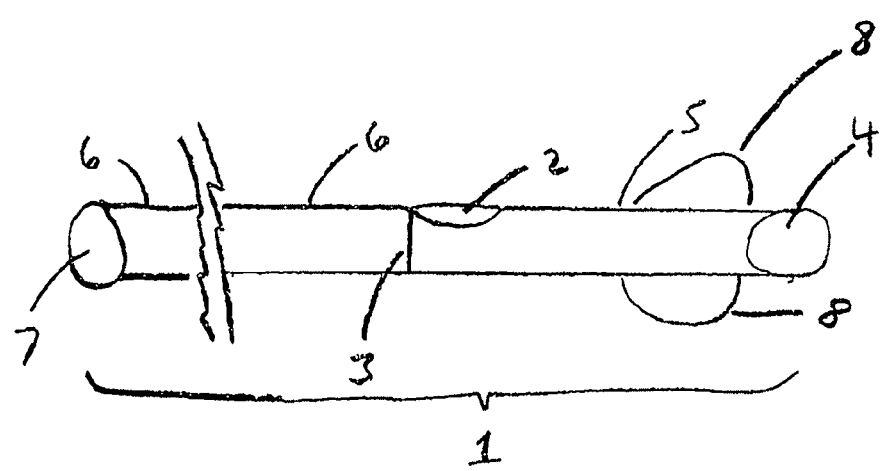
FIG. 1 is a side view of the current invention.

Referring now to FIG. 1, the current invention (1) there is a distal end hole (4) and a side hole (2) disposed upon the outer diameter of the device (1) of the current invention at the juncture of first segment (5) and second segment (6). Side hole (2) defines the end of second segment (6) through proximal end hole (7) from first segment (5) through distal end hole (4). The outer diameter of first segment (5) and second segment (6) are the same in some but not all embodiments.

The bypass catheter device (1) of the current invention is introduced through an incision in a patient's vessel and often directed to a target site by means of standard endovascular techniques, with the aid of wires and/or other delivery catheters, often under fluoroscopic guidance.

Returning to FIG. 1, first segment (5) is used to anchor device (1) so as to position side hole (2) at the desired location. Optionally, first segment (5) may be attached to a balloon (8) which, upon inflation, further anchors device (1) of the current invention in the desired position.

The present invention is positioned such that side hole (2) is positioned to accept blood flow from the patient and direct the blood through first segment (5) out through distal hole (4), bypassing said blood flow past a blockage. The current invention prevents backflow of blood in three ways, or any combination thereof.

FIG. 1 illustrates an embodiment employing valve (3) disposed at the juncture of second section (6) with side hole (2). In this embodiment, once the device (1) of the current invention is positioned in the desired position, valve (3) is closed by the user to prevent blood entering side hole (2) from flowing back into said second segment (6). The blood is thereby directed through first segment (5), through and out end hole (4), and allowed to perfuse the at-risk tissue.

Figure 2:
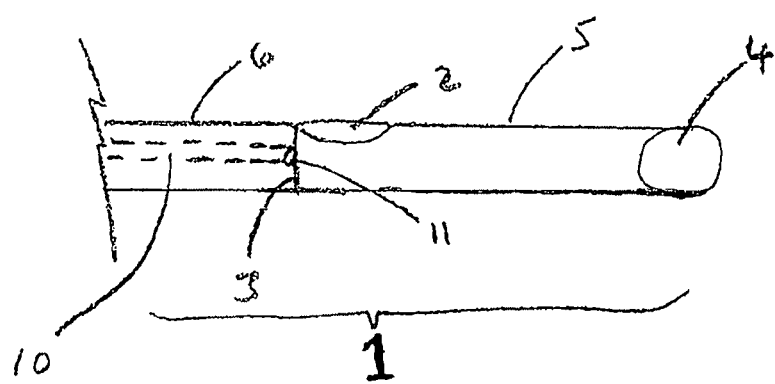
FIG. 2 is a side view of the current invention showing the inner segment with dashed lines.

In an alternative embodiment better depicted in FIG. 2, the inner diameter (10) of second segment (6) is less than the inner diameter of first segment (5). Inner diameter (10) terminates at inner hole (11). Inner hole (11) is smaller than distal end hole (4). The differential acts to constrict backflow and direct blood through first segment (5) to and out end hole (4).

In a preferred embodiment, a valve (3) and a reduced inner diameter (10) and inner hole (11) are employed to constrict backflow of blood.

Figure 3:
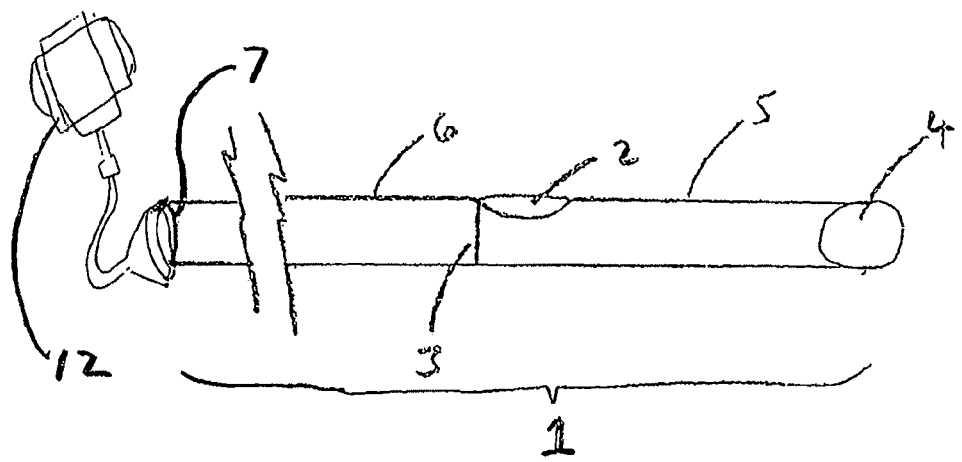
FIG. 3 depicts the first segment of the current invention connected to a pressurized fluid column.

In a still further embodiment depicted in FIG. 3, pressurized fluid may be introduced into second segment (6) to prevent the backflow of blood. FIG. 3 depicts device (1) of the current invention connected to pressurized fluid bag (12) interfacing with proximal end hole (7). Proximal end hole (7) communicates with second segment (6) through to first segment (5). Said pressurized fluid bag (12) may be connected to a flow regulator which is outside the patient's body to allow the user of the current invention to control flow of fluid through the second segment (6).

In another embodiment, pressurized fluid may be used in conjunction with valve (3) and/or inner hole (11) to prevent backflow of blood. In a still further embodiment, pressurized fluid, valve (3) and differential inner diameter (10) and inner hole (11) may be used concurrently.

Figure 4:
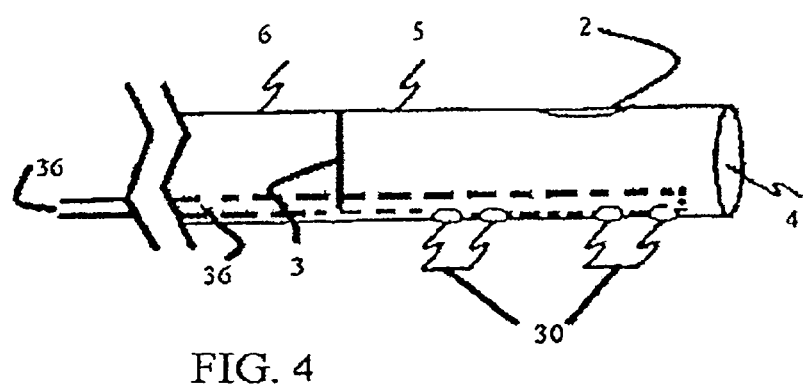
FIG. 4 is a side view of the current invention with perforations allowing infusion of medication from the proximal end.

As shown in FIG. 4, first segment (5) may optionally be perforated with at least one perforation (30).

Perforations (30) are end holes for a lumen which extends from said perforations (30) and communicating with a separate irrigation channel (not shown) disposed at proximal end hole (7) and in communication with an additional controller (36). The fluid typically introduced into the separate channel (36) exiting perforations (30) is designed to dissolve vessel-clogging material. For example, the fluid may be a lytic such as Alteplase, which dissolves blood clots. Said additional controller is capable of sending medication from said additional controller through communicating lumen and out perforations (30) to facilitate the irrigation of clots near first segment (5). Said medication has the capability of softening and/or changing the chemical makeup of clots proximal to perforations (30) for purposes of dislocating and/or dissolving said clot(s) or other blockage. In an alternate embodiment, the present invention device (1) is composed of co-centric lumens wherein perforations (30) communicate with the area between the internal surface of the outer lumen and the outer surface of the inner lumen, said gap extends from perforations (30) to proximal end hole (7) and communicates with said additional controller, allowing medication to be pumped from said additional controller through the area between the internal surface of the outer lumen and the outer surface of the inner lumen and out perforations (30) to allow the infusion of medication to soften, lyse, or alter the composition of clots or blockages. In the preferred embodiment, the inner channel (or area between the internal surface of the outer lumen and the outer surface of the inner lumen) terminates at the most distal perforation (30). Alternatively, the inner channel may terminate in the first segment at or near the end hole (4).

Figure 5:
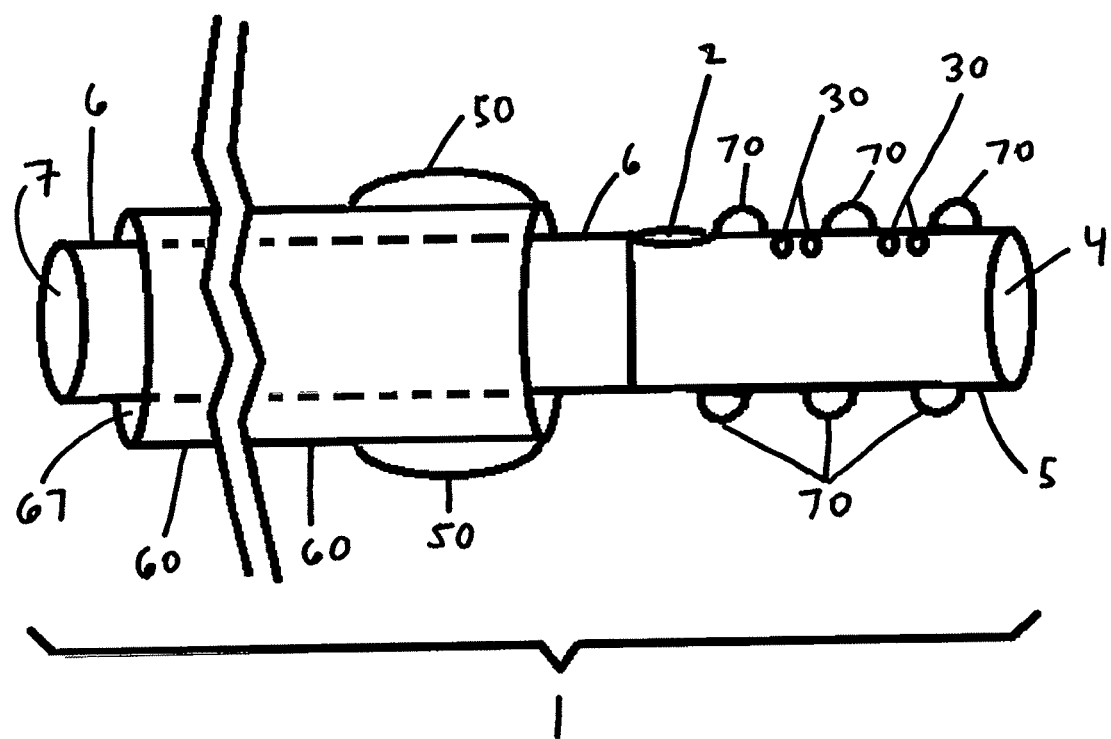
FIG. 5 depicts an alternative embodiment of the current invention.

Referring now to FIG. 5, an alternate embodiment of the device (1) of the present invention further includes rotating, macerating and irrigating elements, more particularly, a slidable outer support sheath (60), macerating elements or loops (70), and/or perforations (30) used as irrigating elements. Said slidable outer support sheath (60) is capable of snugly closing side hole (2) when first segment (5) is withdrawn inside of said sheath (60). This action of withdrawing side hole (2) into outer support sheath (60) results in changing the blood-flow bypass from side hole (2) through distal end hole (4), redirecting the blood flow from distal end hole (4) out proximal end hole (7) due to an aspiration controller communicating with proximal end hole (7). Also shown in this embodiment are optional backflow valve (3) and optional anchoring balloon (50). If the operator chooses to aspirate from distal end hole (4), the bypass catheter (1) can be pulled back so that the side hole (2) is temporarily positioned within sheath (60), which is sized for a snug fit around bypass catheter (1), and aspiration force applied at proximal hole (7) will be transmitted to end hole (4), provided valve (3), when present, is open during said aspiration. It should be noted that for optimal use of this embodiment of the present invention, first segment (5) must fit snugly inside slidable outer support sheath (60).

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. An apparatus for restoring flow in a blocked vessel, comprising:
   (a) a longitudinal structure configured for insertion into a blood vessel,
   (b) said longitudinal structure being adapted to deliver a side hole to a target area,
   (c) said side hole defining a distal first segment and a proximal second segment with a single inner lumen therethrough,
   (d) said first segment having a non-tapered distal end and a distal end hole,
   (e) said second segment having a proximal end and a proximal end hole, and
   (f) said side hole being variably coverable by a slidable outer support sheath, said side hole being adapted for passage of blood therethrough to said distal end hole wherein variable coverage ranges from none to full coverage, and
      wherein when said variable coverage is fully covered, said support sheath is configured to terminate passage of blood therethrough;
   (g) at least one separate tertiary channel extending within the wall of said longitudinal structure from a tertiary proximal end hole to at least one channel exiting perforation, configured to allow injection of fluid therethrough from outside a patient's body,
      wherein an aspirator is reversibly connected to said proximal end hole, thereby allowing aspiration from said distal end hole when said side hole is covered.

2. The apparatus of claim 1, further comprising a balloon disposed on said longitudinal structure.

3. The apparatus of claim 1, further comprising a valve disposed within said longitudinal structure immediately proximal to said side hole.

4. The apparatus of claim 1, wherein the diameter of said lumen in said second segment is less than the diameter that of said first segment.

5. The apparatus of claim 1, further comprising at least external maceration element along said longitudinal structure.

6. The apparatus of claim 5, wherein said at least one maceration element is activated by rotating said longitudinal structure.

7. The apparatus of claim 1, wherein said first segment is sheathed, wherein said slidable sheath supports said first segment and can variably cover said side hole when aspiration via said distal end hole is desired, wherein variably cover ranges from none to full coverage.

8. The apparatus of claim 7, further comprising at least one balloon mounted on said slidable outer support sheath.

9. The apparatus of claim 1, further comprising at least one macerating element disposed upon said first segment distal to said side hole and proximal to said distal end hole.

10. The apparatus of claim 9, wherein said at least one macerating element is disposed distal to said side hole and proximal to said distal end hole upon said first segment, and can rotate with said first segment.

11. The apparatus of claim 1, wherein said second segment is sheathed, wherein said slidable sheath supports said second segment and can cover said side hole, fully, partially, or not at all, when aspiration via said distal end hole is desired.

12. The apparatus of claim 11, further comprising at least one balloon mounted on said slidable outer support sheath.

13. The apparatus of claim 1, capable of simultaneous irrigation via said at least one separate tertiary channel and simultaneous aspiration via said primary end hole and said side hole.

14. The apparatus of claim 1, capable of simultaneous irrigation via said at least one separate tertiary channel and simultaneous aspiration through said single inner lumen and simultaneous maceration.

15. The apparatus of claim 1, further comprising a single balloon proximal to said distal end of said first segment, with at least one secondary lumen designated only to inflate and deflate said balloon that courses through the wall of said longitudinal structure.

16. A method for ameliorating clots in a blood vessel using the apparatus of claim 1, comprising the steps of: (a) inserting distal end of said appartus in said blood vessel; (b) moving said appartus longitudinally along said blood vessel until at least one perforation is distal to a target area, and at least one maceration element is disposed within said target area; (c) positioning said appartus so that said side hole is uncovered and proximal to an intravascular thrombus, and said distal end hole is distal to said thrombus, thereby allowing flow of blood through said longitudinal structure; (d) infusing lytics through said lumen from said tertiary proximal end hole to at least one channel exiting perforation; (e) terminating said infusion; (f) advancing said outer sheath to cover said side hole; (g) attaching an aspirator to said proximal end hole; (h) repositioning said appartus so that said end hole is adjacent to any residual endovascular thrombus; and (i) activating said aspirator and aspirating said residual thrombus.

17. An apparatus for restoring flow in a blocked vessel, comprising:
   (a) a longitudinal structure configured for insertion into a blood vessel,
   (b) said longitudinal structure being adapted to deliver a side hole to a target area, said side hole defining a distal first segment and a proximal second segment with a single inner lumen therethrough,
   (c) said first segment having a non-tapered distal end and a distal end hole,
   (d) said second segment having a proximal end and a proximal end hole,
   (e) said single inner lumen in communication with said distal end hole and said proximal end hole,
   (f) at least one separate tertiary channel extending within the wall of said longitudinal structure from a tertiary proximal end hole to at least one channel exiting perforation, configured to allow injection of fluid therethrough from outside a patient's body,
   (g) said side hole being variably coverable by a slidable outer support sheath,
   (h) said side hole being adapted for passage of blood therethrough to said distal end hole
      wherein variable coverage ranges from none to full coverage, and wherein when said variable coverage is fully covered, said support sheath is configured to terminate flow therethrough, and wherein an aspirator is connected to said proximal end hole, thereby allowing aspiration from said distal end hole.

18. The apparatus of claim 17, further comprising a balloon on said outer support sheath.

19. The apparatus of claim 18, further comprising at least one maceration element on said longitudinal structure.

20. The apparatus of claim 19, wherein said at least one maceration element is activated by rotation of said longitudinal structure.

21. A method of using apparatus of claim 20, comprising the steps of: (a) positioning said apparatus so that said outer support sheath is proximal to said side hole, wherein said side hole is fully open, said side hole is proximal to an intravascular thrombus and said distal end hole is distal to an intravascular thrombus, thereby immediately restoring blood flow into said side hole, through said single inner lumen, and out of said distal end hole; (b) inflating said balloon on said outer support sheath; (c) rotating said longitudinal structure and activating said at least one maceration element (d) stopping rotation (e) pulling said longitudinal structure proximally so that the side hole is covered by said outer support sheath (f) removing said longitudinal structure (g) deflating said balloon; (h) removing said outer support sheath; and (i) obtaining hemostasis.

22. The method of claim 21, further comprising the step of infusing lytics through said tertiary channel immediately after positioning said device.

23. The method of claim 21, further comprising the step of activating said aspirator as said distal end hole is pulled proximally through any residual intravascular thrombus, immediately after pulling said longitudinal structure.

24. The method of claim 21, further comprising the step of connecting an aspirator to the proximal end of said outer sheath and activating said aspirator to remove any residual intraluminal thrombus immediately after removing said longitudinal structure.

* * * * *